US00PP18389P3

(12) United States Plant Patent
Larsen

(10) Patent No.: US PP18,389 P3
(45) Date of Patent: Jan. 1, 2008

(54) *OSTEOSPERMUM* PLANT NAMED 'SUNNY VICTORIA'

(50) Latin Name: *Osteospermum ecklonis*
Varietal Denomination: Sunny Victoria

(75) Inventor: Bjarne N. Larsen, Odense (DK)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/412,308

(22) Filed: Apr. 27, 2006

(65) Prior Publication Data

US 2007/0256204 P1 Nov. 1, 2007

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
*Assistant Examiner*—Annette H Para

(57) ABSTRACT

A new and distinct cultivar of *osteospermum* plant named Sunny Victoria, particularly characterized by spoon-shaped ray florets which generally form an hourglass shape and which when mature are a medium lavender in color at the tips and transition to a very pale lavender to nearly white at the base, upright growth habit, and its nonvariegated leaves.

1 Drawing Sheet

The present invention relates to a new and distinct cultivar of *Osteospermum* plant, botanically known as *Osteospermum ecklonis,* and referred to by the varietal denomination 'Sunny Victoria'.

The new cultivar is the product of a planned breeding program carried out by the inventor in Odense, Denmark. The objective of the breeding program was to create new *osteospermum* cultivars with distinctly new inflorescence colors.

The new cultivar originated from a cross made by the inventor in Odense, Denmark in May 2002. The female, or seed parent, was an unnamed and unpatented proprietary seedling identified by the code number 21.016.00. The characteristics of the female parent are not presently available. The male or pollen parent was the cultivar 'Sunny Cecil', disclosed in U.S. Plant Pat. No. 15,273, and primarily characterized by its compact, upright, mounded plant habit, its dense and bushy growth habit, its freely flowering habit, and its white ray florets and dark purple-tipped disc florets. The new cultivar is distinguished from its male parent by its elliptical ray florets and its different color on the top side of the ray florets.

The first act of asexual reproduction of the new cultivar was accomplished when vegetative cuttings were made from the selection in April 2004 in a controlled environment in Odense, Denmark, by or under the supervision of the inventor.

The new cultivar has not been observed under all possible environmental conditions. The phenotype may vary significantly with variations in environment, such as temperature, light intensity, and day length without, however, any variance in genotype.

SUMMARY OF THE INVENTION

The following traits have been repeatedly observed and have been determined to be basic characteristics of the new cultivar, which in combination distinguish the new cultivar as being new and distinct.

1. The new cultivar has an upright, compact growth habit with short inflorescence stems.
2. Nonvariegated leaves.
3. Spoon-tipped ray florets formed in one or two complete ray floret whorls.
4. The mature upper surface color of the ray florets is lavender at the tips, with the color becoming very pale lavender to nearly white at the base.

Of the many commercial cultivars known to the present inventor(s), the most similar cultivar in comparison to the new cultivar is the commercially available but unpatented cultivar 'Sunny Sonia'. The comparison cultivar similarly has spoon-tipped ray florets, but the ray floret color is a deeper red-purple, and the florets are not very pale lavender to near white at the base.

BRIEF DESCRIPTION OF THE PHOTOGRAPHS

The photograph at the bottom of the sheet shows a front perspective view of typical flowering plants (three) of the new cultivar in an 8" pot. The photograph at the top of the sheet is a view showing in more detail partially and fully open inflorescence of the new cultivar.

The colors in the photographs are as true as it reasonably possible with colored reproductions of this type. If any differences exist between the photographic color and the color values described below, the values in the detailed description are accurate.

DETAILED BOTANICAL DESCRIPTION

In the following description, color references are made to The Royal Horticultural Society Colour Chart. The values are based on plant material grown in Bonsall, Calif., with the plants being very mature and approximately 20 weeks old. The values were taken from one of the three plants shown in the perspective view.

Botanical classification: *Osteospermum ecklonis* cv 'Sunny Victoria'.

Parentage:

*Female parent.*—A proprietary cultivar identified as 21.016.00.

*Male parent.*—'Sunny Cecil'.

Propagation:

*Type.*—Terminal vegetative cuttings.

*Time to initiate roots.*—About 10 to 14 days at 18–20 degrees C.

*Root description.*—Fine, fibrous, and branching.

Plant description:

*General appearance and shape.*—Generally V-shaped profile with a very uniform, rounded canopy.

*Habit.*—Dense foliage, and very free-branching.

*Plant height.*—42 cm.

*Plant diameter or area of spread.*—37 cm. to 48 cm.

*Lateral branching.*—Number of primary lateral branches: 5. Number of secondary lateral branches: 12–15. Length of primary branches: About 37 cm. to 40 cm. Diameter: About 0.6 cm. to 0.8 cm. Internode length: About 1.0 cm. to 1.8 cm. Texture: Smooth, glabrous. Color: 146D.

*Foliage.*—Arrangement: Alternate. Simple or Compound: Simple. Length: About 4.0 cm. to 6.8 cm. Width: About 1.5 cm. to 3.8 cm. Shape: Oblanceolate to obovate. Apex shape: Broadly acute. Base shape: Attenuate. Margin: Nearly entire when young to having narrow, shallow points when mature. Texture: Top is slightly course, and bottom is minutely pubescent. Color: Developing foliage: Upper surface, 137C. Lower surface, 137C. Mature foliage: Upper surface, 147A. Lower surface, 147B. Venation: Upper and lower surfaces, 147A to 147B-C. Petiole: Length, 0.9 to 1.4 cm. Diameter, 0.5 cm. Color: Both upper and lower sections, 147B. Other foliage characteristics: Leaf size and marginal points are highly variable; leaves become much smaller toward shoot tips.

*Inflorescence.*—Appearance: Solitary, terminal, and axillary. Form: Single daisy, actinomorphic. Orientation: Upright if terminal, outward if axillary. Longevity: 5–6 days. Fragrance: A faint sour scent.

*Quantity.*—About 18 open flowers and 30 visible buds on main stem; 2–3 open flowers and 3–4 buds on lateral stems, oriented about 2 degrees to vertical.

*Size.*—Total diameter: 5.7 cm. Depth: About 2.2 cm. Diameter of disc: 1.3 cm. Receptacle diameter: 2.4 cm. Receptacle height: 1.0 cm. Buds (just before anthesis): Height: 1.8 cm. Diameter: 1.2 cm. Shape: Ovoid to pointed. Color: 145A.

*Ray florets.*—Quantity per inflorescence: 22. Shape: Somewhat hourglass-shaped; ligulate with the two margins in the midsections being rolled over top surface. Length: 3.1 cm. Width: 0.5 cm, narrowing to 0.3 cm where margins roll in. Apex: Acute. Base: Acute. Margin: Entire, except for rolled midsections. Texture: Smooth. Aspect: Not completely flat; about 45–60 degrees from vertical. Color: When opening: Upper surface, 75A. Lower surface, 146D at tips and 155D at base. Mature: Upper surface, 75A tips, transitioning to 76D at base. Lower surface 146D at tips, transitioning to 147C and then to 155A at base.

*Disc florets.*—Quantity per inflorescence: Approximately 100. Shape: Tubular. Apex: Acute, 5 pointed. Base: Fused at base. Length: 0.8 cm. Width: 0.25 cm at apex, 0.1 at base. Color: Immature, 93D. Mature, 94B.

*Involucral bracts.*—Quantity per inflorescence: 20. Length: 1.2 cm. Width: 0.2 cm. Shape: Lanceolate. Apex: Acuminate. Base: Truncate. Color: Upper surface, 146C. Lower surface, 146A.

*Peduncles.*—Strength: Good. Aspect: Upright to angle of 30–40 degrees from vertical. Length: Terminal peduncle, 8.4 cm. Fourth peduncle, 1.6 cm. Diameter: About 0.15 cm. Texture: Minutely pubescent. Color: 144B.

*Reproductive organs.*—Androecium: Stamens on disc florets. Stamen number: 5. Anther shape and length: Oblong, 0.3 cm. Anther color: 79A. Pollen color: 23A. Gynoecium: On ray florets only. Pistil length: 0.6 cm. Stigma shape: Bipartite. Stigma color: 86A. Style length: 0.4 cm. Style color: 85B. Seed/fruit: None observed.

Other inflorescence characteristics: The spoon-tipped ray florets result in an inflorescence that is windmill-like when viewed from above. The upward roll of the margins in the midsections of the ray florets is unusual and provides the described hourglass shape. The ray florets are essentially bicolor, transitioning from a medium lavender at the tips to a very pale lavender at the bases. The bright orange-gold outer ring of the disc floret contrasts nicely with the darker center. As the anthers and pollen dehisce from the outer ring toward the center, the pollen shows up as a ring, or bulls-eye, and is an obvious pollination guide.

I claim:

1. A new and distinct cultivar of *osteospermum* plant named Sunny Victoria, as illustrated and described.

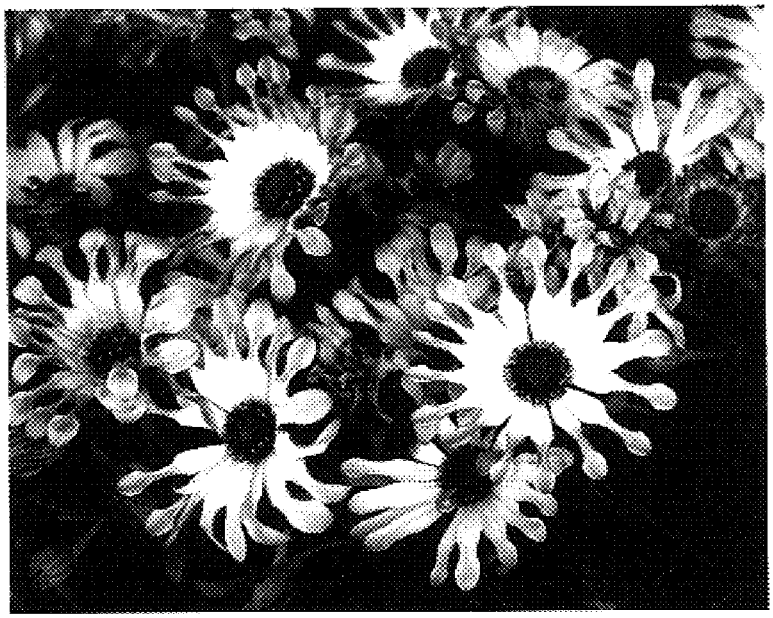
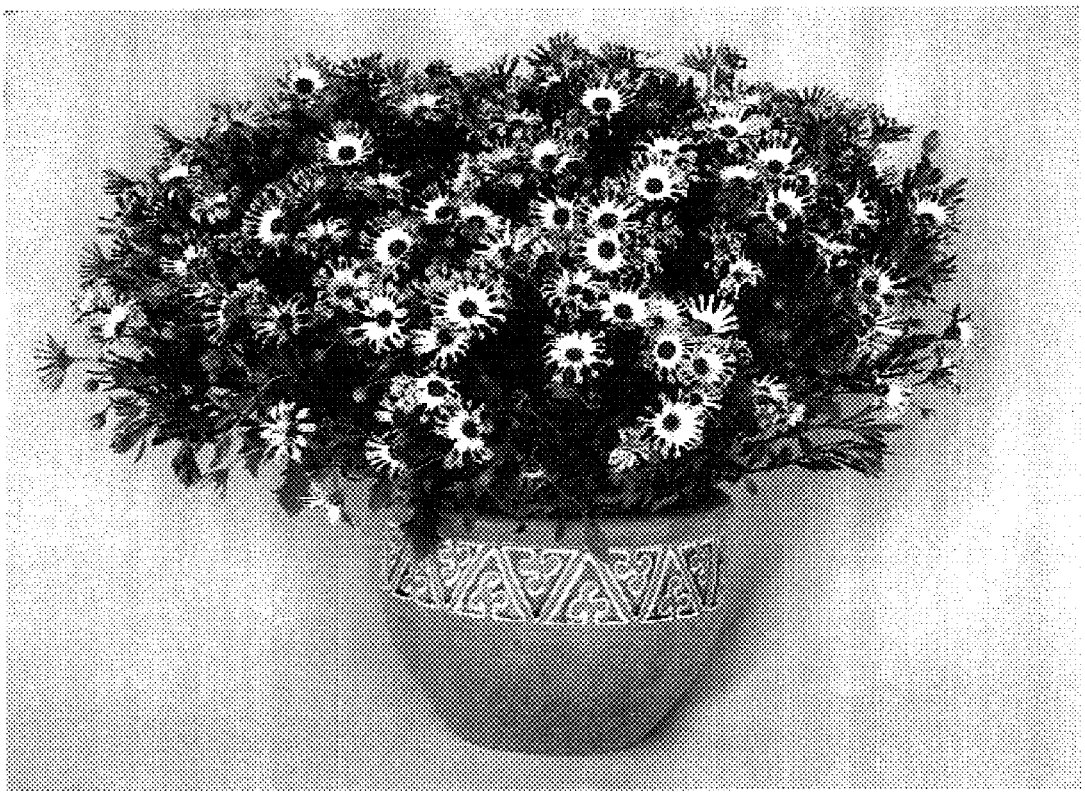

* * * * *